US011231346B2

(12) United States Patent
Akai et al.

(10) Patent No.: US 11,231,346 B2
(45) Date of Patent: Jan. 25, 2022

(54) SPECIMEN PREPARATION APPARATUS

(71) Applicants: JEOL Ltd., Tokyo (JP); National Institute of Advanced Industrial Science and Technology, Tokyo (JP)

(72) Inventors: Satoru Akai, Tokyo (JP); Ayumi Morioka, Tokyo (JP); Nobuo Handa, Tokyo (JP); Akira Kurokawa, Tsukuba (JP); Kazuhiro Kumagai, Tsukuba (JP)

(73) Assignees: JEOL Ltd., Tokyo (JP); National Institute of Advanced Industrial Science, Tokyo (JP)

( * ) Notice: Subject to any disclaimer, the term of this patent is extended or adjusted under 35 U.S.C. 154(b) by 243 days.

(21) Appl. No.: 15/873,246

(22) Filed: Jan. 17, 2018

(65) Prior Publication Data

US 2018/0209879 A1 Jul. 26, 2018

(30) Foreign Application Priority Data

Jan. 20, 2017 (JP) .............................. JP2017-008802

(51) Int. Cl.
*G01N 1/31* (2006.01)
*G01N 35/00* (2006.01)
(Continued)

(52) U.S. Cl.
CPC ................. *G01N 1/31* (2013.01); *G01N 1/28* (2013.01); *G01N 1/4022* (2013.01); *G01N 1/42* (2013.01);
(Continued)

(58) Field of Classification Search
CPC .. G01N 1/31; G01N 1/42; G01N 1/28; G01N 1/4022; G01N 35/00029; G01N 35/00;
(Continued)

(56) References Cited

U.S. PATENT DOCUMENTS 4,567,847 A * 2/1986 Linner ..................... G01N 1/42
118/50.1
4,799,361 A 1/1989 Linner
(Continued)

FOREIGN PATENT DOCUMENTS

JP S63212863 A 9/1988
JP H02171571 A 7/1990
(Continued)

OTHER PUBLICATIONS

Linner et al., "A New Technique for Removal of Amorphous Phase Tissue Water Without Ice Crystal Damage: A Preparative Method for Ultrastructural Analysis and Immunoelectron Miscroscopy", The Journal of Histrochemistry and Cytochemistry, 1986, vol. 34, No. 9, pp. 1123-1135.
European search report for EP patent application No. 18152594.0 dated Jun. 4, 2018.
Notice of Grounds for Rejection issued in JP2017-008802 dated Jun. 9, 2020.

*Primary Examiner* — Jill A Warden
*Assistant Examiner* — Curtis A Thompson
(74) *Attorney, Agent, or Firm* — The Webb Law Firm (57) ABSTRACT

A lower-side structure forms a specimen chamber in which a specimen base is provided. An upper-side structure forms a nozzle chamber above the specimen chamber. The specimen chamber and the nozzle chamber are separated by a gate valve. In the nozzle chamber, at least a tip opening of a nozzle that ejects a specimen is present. A control device maintains a relationship of gas pressures such that a gas pressure in the specimen chamber is higher than a gas pressure in the nozzle chamber when the lower-side structure and the upper-side structure are in communication with each other.

8 Claims, 6 Drawing Sheets

(51) Int. Cl.
*G01N 1/40* (2006.01)
*G01N 1/28* (2006.01)
*G01N 1/42* (2006.01)
*B01D 1/24* (2006.01)
*G01N 1/00* (2006.01)
*B65B 3/04* (2006.01)
*B65B 1/04* (2006.01)
*G01N 35/10* (2006.01)
*G01N 33/487* (2006.01)
*B01L 3/00* (2006.01)
*G01N 1/20* (2006.01)
*G01N 1/30* (2006.01)

(52) U.S. Cl.
CPC ......... G01N 35/00029 (2013.01); *B01D 1/24* (2013.01); *B01L 3/00* (2013.01); *B65B 1/04* (2013.01); *B65B 3/04* (2013.01); *G01N 1/00* (2013.01); *G01N 33/487* (2013.01); *G01N 35/00* (2013.01); *G01N 35/00732* (2013.01); *G01N 35/10* (2013.01); *G01N 2001/2057* (2013.01); *G01N 2001/302* (2013.01); *G01N 2001/4027* (2013.01); *G01N 2001/4033* (2013.01)

(58) Field of Classification Search
CPC ........ G01N 33/487; G01N 35/10; G01N 1/00; G01N 2001/4033; G01N 2001/4027; G01N 2001/302; G01N 2001/2057; G01N 35/00732; B01L 3/00; B65B 1/04; B65B 3/04; B01D 1/24
See application file for complete search history.

(56) References Cited

U.S. PATENT DOCUMENTS

| | | | |
|---|---|---|---|
| 5,044,165 A * | 9/1991 | Linner | B01D 8/00 118/50.1 |
| 5,364,756 A | 11/1994 | Livesey et al. | |
| 2005/0188705 A1* | 9/2005 | Jones | A01N 1/02 62/86 |
| 2008/0057577 A1* | 3/2008 | Arnold | C07K 14/32 435/348 |
| 2008/0293832 A1* | 11/2008 | Yokoi | G01N 1/42 516/98 |
| 2009/0191097 A1* | 7/2009 | Hanafusa | B01L 3/0217 422/400 |
| 2013/0134325 A1* | 5/2013 | Negishi | G01N 1/32 250/428 |
| 2014/0178858 A1* | 6/2014 | Reinhardt | B01L 9/52 435/5 |
| 2014/0209193 A1* | 7/2014 | Matsushita | H01J 37/185 137/565.13 |
| 2015/0137000 A1* | 5/2015 | Naruse | H01J 37/20 250/441.11 |
| 2015/0137001 A1* | 5/2015 | Hiroki | H01J 37/18 250/441.11 |

FOREIGN PATENT DOCUMENTS

| | | | | |
|---|---|---|---|---|
| JP | H0513358 B2 * | 5/1993 | | G01N 1/28 |
| JP | H05126696 A | 5/1993 | | |
| JP | 3056846 B2 | 4/2000 | | |
| JP | 2007322291 A | 12/2007 | | |
| JP | 2010008141 A | 1/2010 | | |
| JP | 2015141083 A | 8/2015 | | |

* cited by examiner

SPECIMEN PREPARATION APPARATUS

CROSS REFERENCE TO RELATED APPLICATION

The disclosure of Japanese Patent Application No. 2017-008802 filed on Jan. 20, 2017, including the specification, claims, drawings, and abstract, is incorporated herein by reference in its entirety.

TECHNICAL FIELD

The present disclosure relates to a technique for preparing a specimen for a microscope.

BACKGROUND

There are some cases where a microparticle specimen to be observed by a microscope such as an electron microscope is prepared from a liquid drop having a solution in which the microparticles are dispersed in a solvent as an undiluted solution (hereinafter, referred to as "microparticle dispersed liquid drop"). For example, there is known a technique in which the microparticle dispersed liquid drop is dropped onto a cooled specimen base and is cooled (for example, the liquid drop is solidified), and the solvent of the liquid drop is dried in this state to prepare the microparticle specimen (as disclosed in, for example, JP 2015-141083 A).

Depending on the environment, dew condensation may occur on the specimen base or the like during the preparation process of the specimen, and the specimen may be contaminated by a contaminating substance in water produced by the dew condensation.

An advantage of the present disclosure lies in prevention of occurrence of the dew condensation on the specimen base or the like in cases where the specimen is prepared by drying the solvent of the liquid drop in which the specimen is dispersed.

SUMMARY

According to one aspect of the present disclosure, there is provided a specimen preparation apparatus comprising: a lower-side structure that forms a specimen chamber in which a specimen base is provided; an upper-side structure that forms a nozzle chamber above the specimen chamber; a gate valve that separates the specimen chamber and the nozzle chamber; and a controller that controls a gas pressure in the specimen chamber, wherein at least a nozzle tip opening of a nozzle that ejects a specimen is present in the nozzle chamber, and the controller maintains a relationship of gas pressures such that a gas pressure in the specimen chamber is higher than a gas pressure in the nozzle chamber when the lower-side structure and the upper-side structure are in communication with each other.

According to the above-described structure, because the gas pressure in the specimen chamber is higher than the gas pressure in the nozzle chamber, intrusion of air from the nozzle chamber into the specimen chamber can be prevented or suppressed. With such a configuration, even when the temperature in the specimen chamber is reduced by cooling the inside of the specimen chamber, occurrence of dew condensation at the specimen base or the like can be prevented. When the specimen is prepared, the gate valve is opened, and the nozzle is transported from the nozzle chamber into the specimen chamber. On the specimen base, for example, a specimen holder is placed, and a liquid drop is ejected from the nozzle tip opening to the specimen holder. In the liquid drop, the specimen (for example, a microparticle) is dispersed. For example, a pressure of the specimen chamber is reduced by a vacuum pump so that the solvent of the liquid drop is dried and the specimen (for example, a microparticle specimen) remains on the specimen holder.

According to another aspect of the present disclosure, a period in which the lower-side structure and the upper-side structure are in communication with each other may be a period included in a process of dropping the specimen onto the specimen base.

According to another aspect of the present disclosure, the controller may control supply of a drying gas into the specimen chamber such that the gas pressure in the specimen chamber is higher than the gas pressure in the nozzle chamber.

According to another aspect of the present disclosure, the controller may maintain the relationship of the gas pressures between the specimen chamber and the nozzle chamber by supplying the drying gas into the specimen chamber after the gate valve is opened. With this configuration, even when the gate valve is opened and the specimen chamber and the nozzle chamber are connected to each other, the gas pressure in the specimen chamber can be maintained at a higher pressure than the gas pressure in the nozzle chamber.

According to another aspect of the present disclosure, the specimen preparation apparatus may further comprise a cooler that cools the specimen base, and the controller may control the gas pressures such that the gas pressure in the specimen chamber is higher than the gas pressure in the nozzle chamber after the specimen base is cooled by the cooler and before the gate valve is opened.

According to another aspect of the present disclosure, the specimen preparation apparatus may further comprise a vacuum device that reduces a pressure in the specimen chamber, and the controller may open the gate valve after reducing the pressure in the specimen chamber by the vacuum device, cooling the specimen base by the cooler, supplying the drying gas into the specimen chamber, and then forming the relationship of the gas pressures between the specimen chamber and the nozzle chamber, in a state where the gate valve is closed.

According to another aspect of the present disclosure, the specimen preparation apparatus may further comprise a transport mechanism that transports the nozzle between the upper-side structure and the lower-side structure, and the upper-side structure may comprise a deformation member that deforms with a movement of the nozzle.

According to another aspect of the present disclosure, the specimen preparation apparatus may further comprise a hard frame that is placed to surround an opening of the gate valve at a periphery of the gate valve, and the deformation member may be a bag-shaped member which seals from an opening edge of the frame to a periphery of the nozzle.

According to the above-described structure, with the frame, it becomes possible to prevent entry or dragging of the deformation member into the specimen chamber. For example, the nozzle chamber is formed by the deformation member.

According to another aspect of the present disclosure, the controller may further control a process of dropping the specimen onto the specimen base by the nozzle, and a process of executing vacuum-drying by reducing a pressure in the specimen chamber after the specimen is dropped onto the specimen base.

Advantageous Effects of Invention

According to the present disclosure, it becomes possible to prevent occurrence of the dew condensation at the specimen base or the like in a case where the specimen is prepared by drying the solvent of the liquid drop in which the specimen is dispersed.

BRIEF DESCRIPTION OF DRAWINGS

Embodiment(s) of the present disclosure will be described by reference to the following figures, wherein.

DESCRIPTION OF EMBODIMENTS

First Embodiment

Figure 1:
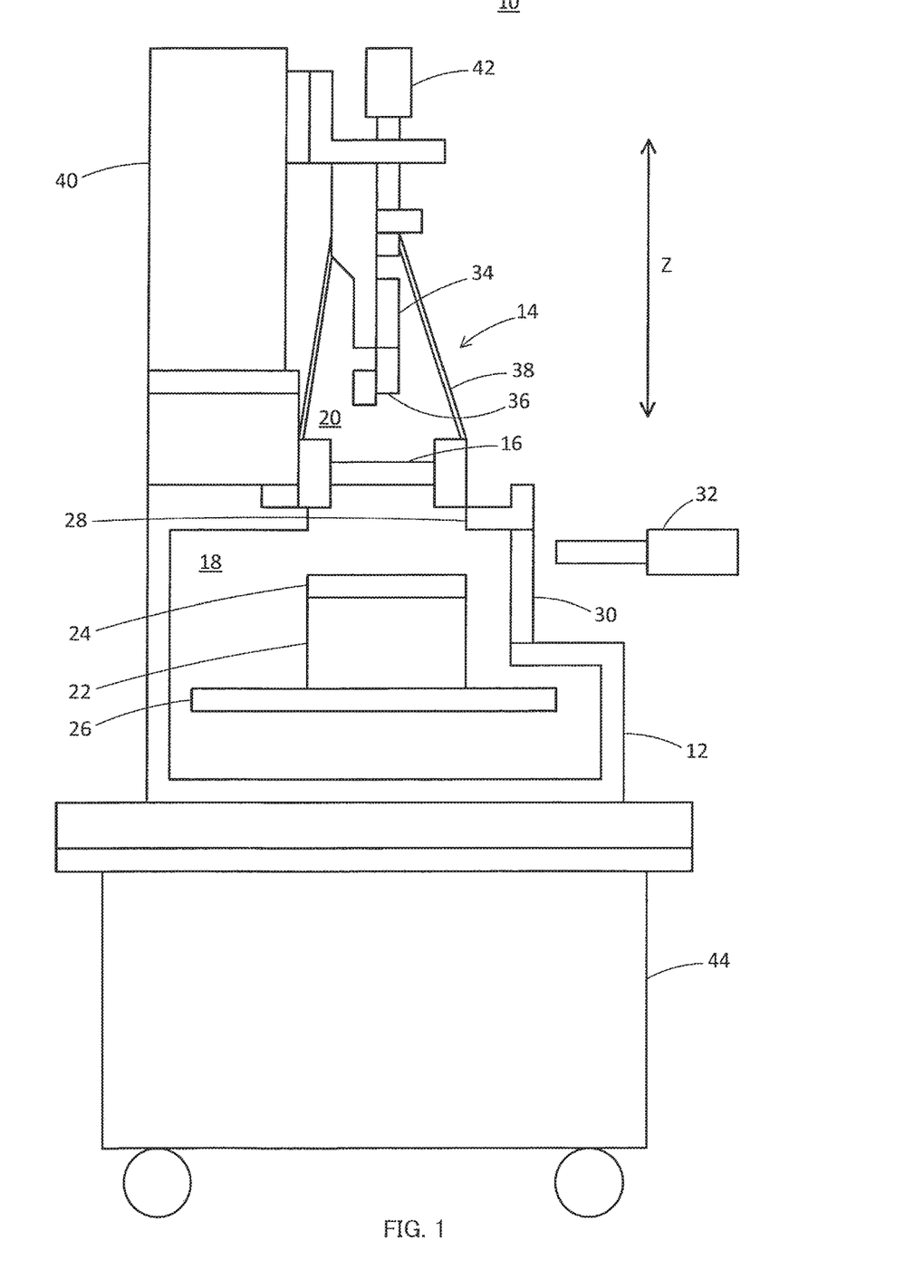
FIG. 1 is a diagram showing a specimen preparation apparatus according to a first embodiment of the present disclosure.

A specimen preparation apparatus according to a first embodiment of the present disclosure will now be described. FIG. 1 schematically shows a structure of a specimen preparation apparatus 10 according to the first embodiment of the present disclosure. The specimen preparation apparatus 10 is an apparatus which prepares a specimen to be observed by a microscope. The specimen preparation apparatus 10 is, for example, a specimen cooling and drying apparatus, and prepares a microparticle specimen by cooling a liquid drop having a solution in which microparticles are dispersed in a solvent as an undiluted solution (hereinafter, referred to as "microparticle dispersed liquid drop") and drying the solvent of the liquid drop.

The microparticle to be observed is a microparticle, for example, having a particle size (for example, a length of a shortest portion of the microparticle) in a range of 1 nm~100 μm. Alternatively, particles having particle sizes outside of this range may be used as the particle to be observed. A volume of the microparticle dispersed liquid drop is, for example, about 1 pL (pico-liter). Alternatively, the volume of the microparticle dispersed liquid drop may be other than 1 pL. As the solvent of the liquid drop, for example, water, ethanol, methanol, or the like is used. Alternatively solvents other than these may be used.

The microscope is, for example, a microscope which uses an electron beam, an ion beam, or the like, and is, for example, a transmission electron microscope (TEM), a scanning electron microscope (SEM), a scanning transmission electron microscope (STEM), an atomic force microscope (AFM), a scanning probe microscope (SPM), a scanning tunnel microscope (STM), a helium ion microscope (HIM), an optical microscope which uses light and laser, or the like.

The specimen preparation apparatus 10 generally includes a lower-side structure 12, an upper-side structure 14 provided above the lower-side structure 12, and a gate valve 16. The lower-side structure 12 is a member in the inside of which a specimen chamber 18 is formed. The lower-side structure 12 is, for example, a vacuum chamber, and the specimen chamber 18 is a space having airtightness. The upper-side structure 14 is a member in the inside of which a nozzle chamber 20 is formed. The nozzle chamber 20 is formed above the specimen chamber 18. The nozzle chamber 20 is, for example, a simple space, and is not a completely airtight chamber. The gate valve 16 is a member which performs an open and close operation, is provided between the lower-side structure 12 and the upper-side structure 14, and is a member which separates the specimen chamber 18 and the nozzle chamber 20 (a movable separation member). In a state where the gate valve 16 is closed, the specimen chamber 18 and the nozzle chamber 20 are separated by the gate valve 16, and in a state where the gate valve 16 is open, the specimen chamber 18 and the nozzle chamber 20 are in communication with each other (connected to each other). In the example configuration of FIG. 1, the gate valve 16 is closed, and thus, the specimen chamber 18 and the nozzle chamber 20 are separated. In the state where the gate valve 16 is closed, the specimen chamber 18 is in a tightly sealed state.

In the specimen chamber 18, a specimen holder base 22 is provided. On the specimen holder base 22, a specimen holder 24 onto which the microparticle dispersed liquid drop is dropped is placed. On the specimen holder 24, for example, a plurality of pores, fine channels, or the like are in a regular arrangement such as a grid shape, an array shape, or a honeycomb shape, or an electron microscope grid mesh or a grid mesh with a support membrane is mounted on the specimen holder 24. The microparticle dispersed liquid drop is dropped onto individual pores or fine channels. Alternatively, the specimen holder 24 may be a member having another shape such as a substrate. The specimen holder base 22 and the specimen holder 24 are formed from, for example, a material such as a metal such as aluminum, copper, or the like, fine ceramics, or the like, and a part of the specimen holder 24 may be formed by a thin film of an organic substance. In other words, the specimen holder base 22 and the specimen holder 24 may be formed by any material, so long as the material does not obstruct heat conduction. The specimen holder base 22 is provided on a specimen cooling member 26. The specimen cooling member 26 is a member for cooling the microparticle dispersed liquid drop dropped onto the specimen holder 24, and cools the microparticle dispersed liquid drop using, for example, a Peltier element. The microparticle dispersed liquid drop is cooled to, for example, a temperature of about −40° C.~−20° C. by the specimen cooling member 26. Alternatively, the microparticle dispersed liquid drop may be cooled by other methods. The specimen holder base 22, the specimen holder 24, and the specimen cooling member 26 collectively form, for example, a "specimen base."

An opening 28 is formed at an upper part of the lower-side structure 12. In the state where the gate valve 16 is open, the specimen chamber 18 and the nozzle chamber 20 are in communication with each other through the opening 28.

In addition, a transparent window 30 (for example, a glass window) may be provided on a side surface of the lower-side structure 12. A camera 32 is placed at an outer side of the lower-side structure 12, and the camera 32 images the inside of the specimen chamber 18 through the window 30. For example, the microparticle dispersed liquid drop dropped onto the specimen holder 24 is imaged by the camera 32, so that an operator can observe the state of the microparticle dispersed liquid drop and the specimen holder 24, or the like. For example, the operator can check whether or not there is an occurrence of the dew condensation.

The lower-side structure 12 is formed from, for example, a metal such as aluminum, copper, or the like. Alternatively, the lower-side structure 12 may be formed from other materials.

At least a tip opening 36 of a nozzle 34 is present in the nozzle chamber 20. In other words, the tip opening 36 is placed in the nozzle chamber 20. Alternatively, the entirety of the nozzle 34 may be placed in the nozzle chamber 20. The nozzle 34 is, for example, an inkjet nozzle. A solution in which the microparticle is dispersed is supplied from a solution supply system (not shown) to the nozzle 34, and the nozzle 34 ejects the microparticle dispersed liquid drop from the tip opening 36. The nozzle 34 is movable at least in the up-and-down direction (Z direction) by a transport mechanism 40 to be described later.

The upper-side structure 14 includes a cover member 38 serving as a deformation member which deforms with a movement of the nozzle 34. The cover member 38 is, for example, a bag-shaped member which surrounds and seals from an opening edge of the gate valve 16 to a periphery of the nozzle 34. A space surrounded by the cover member 38 corresponds to the nozzle chamber 20. Alternatively, the cover member 38 may be a member having a shape other than the bag shape; for example, the cover member 38 may be a bellows-shaped member which deforms with the movement of the nozzle 34. The cover member 38 is formed from, for example, a material having elasticity (for example, a resin).

The specimen preparation apparatus 10 also comprises the transport mechanism 40. The transport mechanism 40 is a mechanism which transports the nozzle 34 in at least the up-and-down direction (Z direction). The transport mechanism 40 transports the nozzle 34 between the lower-side structure 12 and the upper-side structure 14 by transporting, for example, the nozzle 34 in the up-and-down direction. Alternatively, the transport mechanism 40 may have functions to transport the nozzle 34 in a plurality of directions orthogonal to the up-and-down direction (Z direction) (for example, a left-and-right direction (X direction), and a front-and-rear direction (Y direction)). The X direction, the Y direction, and the Z direction are directions orthogonal to each other.

A camera 42 is provided above the nozzle 34. With the camera 42, it becomes possible to image the nozzle chamber 20 from above the chamber, and the specimen chamber 18 can be imaged from above the chamber in the state where the gate valve 16 is open.

The specimen preparation apparatus 10 may be placed on a platform truck 44 such as a storage rack or the like. In the platform truck 44, for example, there may be stored a control device which controls the ejection operation of the microparticle dispersed liquid drop by the nozzle 34, the transport operation of the nozzle 34 by the transport mechanism 40, or the like. Alternatively, the specimen preparation apparatus 10 may be placed on the floor or the like, and not on the platform truck 44.

Figure 2:
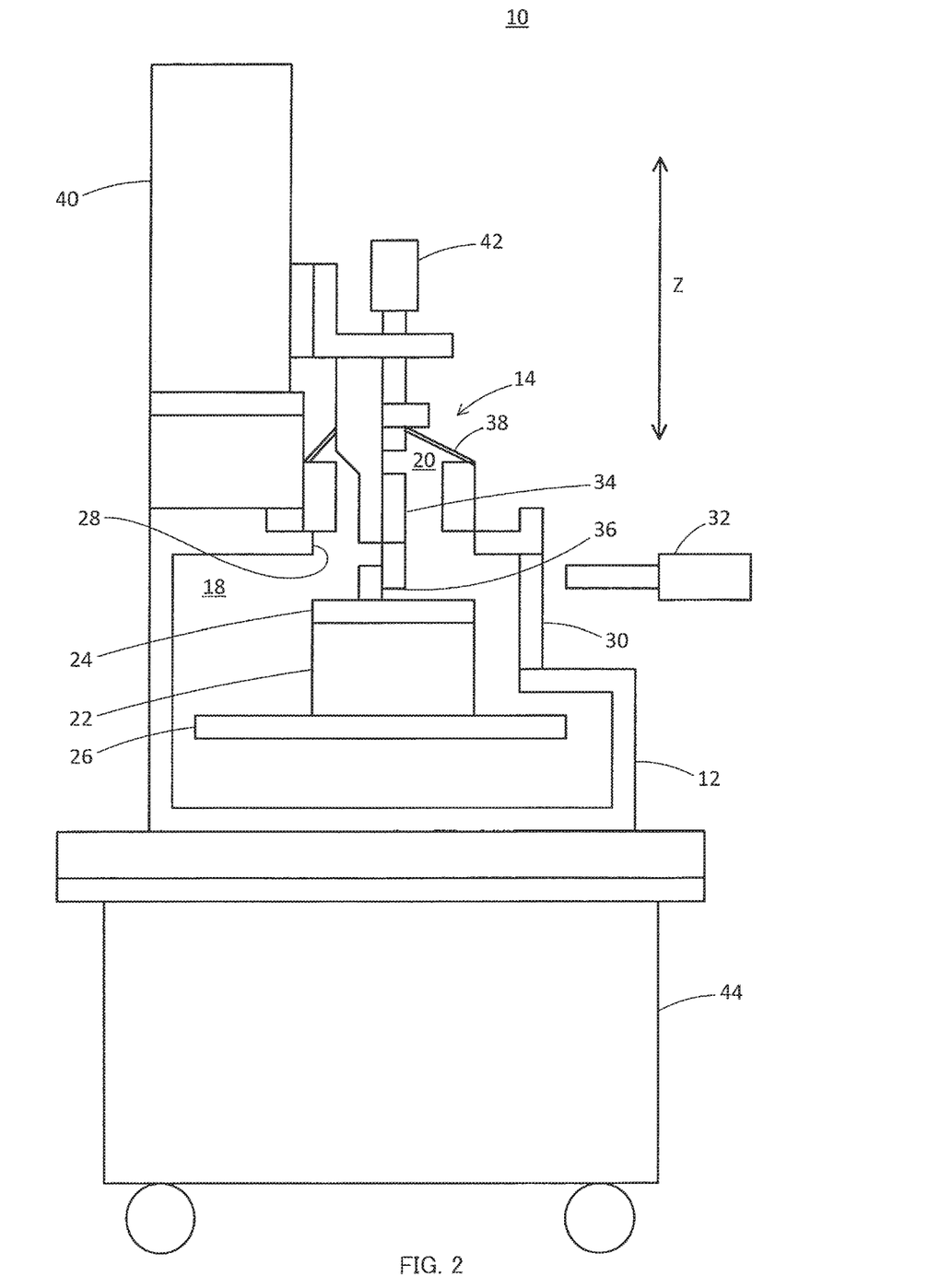
FIG. 2 is a diagram showing the specimen preparation apparatus according to the first embodiment of the present disclosure.

When the microparticle dispersed liquid drop is dropped onto the specimen holder 24, as shown in FIG. 2, the gate valve 16 is opened so that the specimen chamber 18 and the nozzle chamber 20 are connected to each other, and, in this state, the nozzle 34 is transported from the nozzle chamber 20 into the specimen chamber 18 by the transport mechanism 40. In this process, with the movement of the nozzle 34, the cover member 38 is deformed (for example, folded). The nozzle 34 is transported until the tip opening 36 of the nozzle 34 is placed near the specimen holder 24, and, in this state, the nozzle 34 ejects the microparticle dispersed liquid drop from the tip opening 36 onto the specimen holder 24. With this process, the microparticle dispersed liquid drop is dropped onto the specimen holder 24. For example, while the nozzle 34 is moved in the X and Y directions by the transport mechanism 40, the microparticle dispersed liquid drop is ejected from the nozzle 34, to drop a plurality of the microparticle dispersed liquid drops onto the specimen holder 24. For example, the microparticle dispersed liquid drops are dropped into the plurality of pores and fine channels formed in the grid shape. The microparticle dispersed liquid drop dropped onto the specimen holder 24 is frozen by the specimen cooling member 26.

After the dropping of the microparticle dispersed liquid crop is completed, the nozzle 34 is transported from inside of the specimen chamber 18 into the nozzle chamber 20 by the transport mechanism 40. After the transport is completed, the gate valve 16 is closed. In this state, the pressure inside the specimen chamber 18 is reduced by a vacuum pump, and the inside of the specimen chamber 18 is set in a vacuum state. With this process, vacuum-drying is executed. The solvent of the microparticle dispersed liquid drop is evaporated (frozen solvent is sublimated), and the microparticle remains in the specimen holder 24. The remaining microparticle is used as the specimen for the microscope. Alternatively, depending on the observation condition by the microscope, the solvent may also remain.

Figure 3:
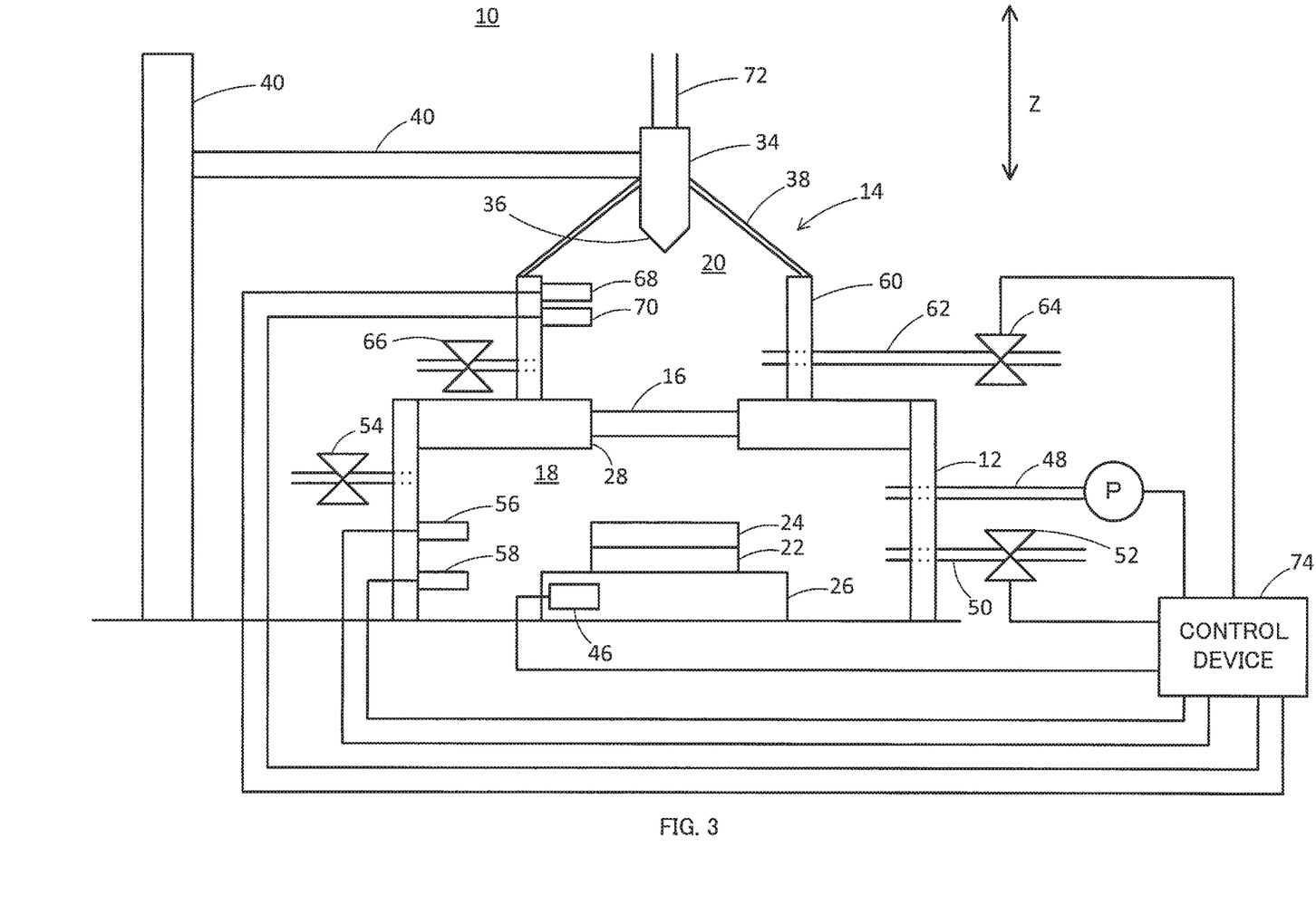
FIG. 3 is a diagram showing the specimen preparation apparatus according to the first embodiment of the present disclosure.

The structure of the specimen preparation apparatus 10 will now be described in further detail with reference to FIG. 3. FIG. 3 shows a more detailed structure of the specimen preparation apparatus 10, and pipes or the like are shown in addition to the structure of the specimen preparation apparatus 10 shown in FIG. 1.

Similar to the structure shown in FIG. 1, the specimen preparation apparatus 10 comprises the lower-side structure 12, the upper-side structure 14, the gate valve 16, and the nozzle 34. In the lower-side structure 12, the specimen chamber 18 is formed, and the specimen cooling member 26 is placed in the specimen chamber 18. During preparation of the specimen, the specimen holder base 22 is placed on the specimen cooling member 26, and the specimen holder 24 is placed on the specimen holder base 22. The upper-side structure 14 includes the cover member 38, and the nozzle chamber 20 is formed in the upper-side structure 14. In the nozzle chamber 20, at least the tip opening 36 of the nozzle 34 is present. In the example configuration shown in FIG. 3, the gate valve 16 is closed, and thus, the specimen chamber 18 and the nozzle chamber 20 are separated. In the state where the gate valve 16 is open, the specimen chamber 18 and the nozzle chamber 20 are in communication with each other (connected to each other) through the opening 28 of the lower-side structure 12. The nozzle 34 is transported in the X direction, the Y direction, and the Z direction by the transport mechanism 40. Although not shown in FIG. 3, the window 30 may be provided on the lower-side structure 12 and the inside of the specimen chamber 18 may be imaged by the camera 32, as shown in FIG. 1. Further, the inside of the specimen chamber 18 may be imaged from above the chamber by the camera 42.

A temperature sensor 46 is provided on the specimen cooling member 26. The temperature sensor 46 measures a temperature of the specimen cooling member 26. A measurement value of the temperature sensor 46 (temperature data) is output to a control device 74 to be described later. For example, the temperature of the specimen cooling member 26 is controlled by reference to the measurement value of the temperature sensor 46.

A vacuum pipe 48 is provided in the lower-side structure 12. One end of the vacuum pipe 48 is placed in the specimen chamber 18, and the other end is connected to a vacuum pump P. In the vacuum-drying, the pressure in the specimen chamber 18 is reduced by the vacuum pump P. For example, the pressure after the pressure reduction is about 20 Pa to 0.1 Pa. The numerical values described herein are merely exemplary, and the degree of pressure reduction may be adjusted according to the conditions of the specimen preparation.

In addition, a drying gas pipe 50 is provided in the lower-side structure 12. One end of the drying gas pipe 50 is placed in the specimen chamber 18, and the other end is connected to a drying gas supply system (not shown). The drying gas supplied from the drying gas supply system is supplied to the specimen chamber 18 through the drying gas pipe 50. As the drying gas, a gas having a lower dew-point temperature than a reaching temperature of the specimen base, for example, nitrogen gas, inert gas such as argon gas, dry air, or the like, may be used. An electromagnetic valve 52 is provided on the drying gas pipe 50, and the amount of supply of the drying gas into the specimen chamber 18 can be adjusted by controlling open and close states of the electromagnetic valve 52. The control to open and close the electromagnetic valve 52 is achieved by the control device 74 to be described later.

Moreover, a relief valve 54 is provided on the lower-side structure 12. When the pressure in the specimen chamber 18 becomes greater than or equal to a preset pressure (a first setting pressure), the relief valve 54 is opened, and the gas in the specimen chamber 18 is discharged to the outside of the specimen chamber 18. When the pressure in the specimen chamber 18 is lower than the first setting pressure, the relief valve 54 is closed.

A temperature and humidity sensor 56 and a pressure sensor 58 may be provided in the specimen chamber 18. For example, the temperature and humidity sensor 56 and the pressure sensor 58 are attached on an inner side surface of the lower-side structure 12 in the specimen chamber 18. The temperature and humidity sensor 56 measures a temperature and a humidity in the specimen chamber 18, and the pressure sensor 58 measures a pressure in the specimen chamber 18. Measurement values of the temperature and humidity sensor 56 (temperature data and humidity data), and a measurement value of the pressure sensor 58 (pressure data) are output to the control device 74 to be described later. For example, the amount of the drying gas to be supplied into the specimen chamber 18 may be controlled based on the measurement values of the temperature and humidity sensor 56 and the measurement value of the pressure sensor 58.

The upper-side structure 14 includes a hard frame 60 in addition to the cover member 38. The frame 60 is provided almost vertically to surround the opening 28 and the opening of the gate valve 16 at a periphery of the gate valve 16. The cover member 38 surrounds and seals from the opening edge at an upper-side of the frame 60 to the periphery of the nozzle 34. With the use of the frame 60, when the nozzle 34 is transported into the specimen chamber 18, it becomes possible to prevent entry of the cover member 38 to a position where the cover member 38 obstructs ejection of the liquid drop from the tip opening 36 of the nozzle 34. A space surrounded by the cover member 38 and the frame 60 corresponds to the nozzle chamber 20. Alternatively, the frame 60 may be omitted. In this case, the cover member 38 surrounds and seals from the opening edge of the gate valve 16 to the periphery of the nozzle 34, and a space surrounded by the cover member 38 corresponds to the nozzle chamber 20.

A drying gas pipe 62 is placed on the frame 60. One end of the drying gas pipe 62 is placed in the nozzle chamber 20, and the other end is connected to the drying gas supply system (not shown). The drying gas supplied from the drying gas supply system is supplied into the nozzle chamber 20 through the drying gas pipe 62. An electromagnetic valve 64 is provided on the drying gas pipe 62, and the amount of supply of the drying gas into the nozzle chamber 20 can be adjusted by controlling the open and close states of the electromagnetic valve 64. The control of the opening and closing of the electromagnetic valve 64 is executed by the control device 74 to be described later.

A relief valve 66 is provided on the frame 60. When a pressure in the nozzle chamber 20 becomes greater than or equal to a preset pressure (a second setting pressure), the relief valve 66 is opened, and the gas in the nozzle chamber 20 is discharged to the outside of the nozzle chamber 20. When the pressure in the nozzle chamber 20 is lower than the second setting pressure, the relief valve 66 is closed. The second setting pressure for the relief valve 66 provided in the nozzle chamber 20 is lower than the first setting pressure for the relief valve 54 provided in the specimen chamber 18 (first setting pressure>second setting pressure). With this configuration, the relief valve 66 in the nozzle chamber 20 functions to discharge the gas to the outside at a lower pressure than that for the relief valve 54 in the specimen chamber 18. Therefore, it becomes possible to maintain a gas pressure in the specimen chamber 18 at a higher gas pressure than a gas pressure in the nozzle chamber 20 during supply of the drying gas.

In the nozzle chamber 20, a temperature and humidity sensor 68 and a pressure sensor 70 may be provided. For example, the temperature and humidity sensor 68 and the pressure sensor 70 are attached on an inner side surface of the frame 60 in the nozzle chamber 20. The temperature and humidity sensor 68 measures a temperature and a humidity in the nozzle chamber 20, and the pressure sensor 70 measures a pressure in the nozzle chamber 20. Measurement values of the temperature and humidity sensor 68 (temperature data and humidity data), and a measurement value of the pressure sensor 70 (pressure data) are output to the control device 74 to be described later. For example, the amount of the drying gas to be supplied into the nozzle chamber 20 may be controlled based on the measurement values of the temperature and humidity sensor 68 and the measurement value of the pressure sensor 70.

A specimen supply pipe 72 is connected to the nozzle 34. A solution in which a microparticle is dispersed in a solvent is supplied from a specimen supply system (not shown) to the nozzle 34 through the specimen supply pipe 72. The nozzle 34 receives the solution supplied from the specimen supply system, and ejects the microparticle dispersed liquid drop. The ejection operation of the microparticle dispersed liquid drop is controlled by the control device 74 to be described later.

The control device 74 is a device which controls the opening and closing of the gate valve 16, the cooling operation by the specimen cooling member 26, the ejection operation of the liquid drop by the nozzle 34, the transport operation by the transport mechanism 40, the operation of the pump P, the opening and closing of the electromagnetic valves 52 and 64, or the like. The control device 74 controls the operations of respective units according to the stages of the specimen preparation, for example. Alternatively, the control device 74 may control the opening and closing of the electromagnetic valves 52 and 64 based on the measurement values of the temperature and humidity sensors 56 and 68, and the measurement values of the pressure sensors 58 and 70. The control device 74 comprises, for example, a processor such as a CPU and a storage device which stores a program (such as, for example, a memory, a hard disk drive, or the like), and the control by the control device 74 is realized by the processor reading and executing the program. Alternatively, the control device 74 may be formed by hardware circuits.

The control device 74 controls the gas pressure, for example, such that the pressure in the specimen chamber 18 (gas pressure) is higher than the pressure in the nozzle chamber 20 (gas pressure). For example, the control device 74 controls the amount of drying gas supplied into the specimen chamber 18 such that the gas pressure in the specimen chamber 18 is higher than the gas pressure in the nozzle chamber 20. More specifically, the control device 74 controls the amount of drying gas such that the gas pressure in the specimen chamber 18 is higher than the gas pressure in the nozzle chamber 20 in a state where the specimen holder base 22 and the specimen holder 24 are cooled by the specimen cooling member 26, and before the gate valve 16 is opened. Further specifically, the control device 74 reduces the pressure in the specimen chamber 18 by the vacuum pump P (sets a vacuum state) in the state where the gate valve 16 is closed, and then cools the specimen holder base 22 and the specimen holder 24 by the specimen cooling member 26. When the microparticle dispersed liquid drop is dropped onto the specimen holder 24, the control device 74 introduces the drying gas into the specimen chamber 18 in this state. The control device 74 opens the gate valve 16 after the gas pressure in the specimen chamber 18 becomes higher than the gas pressure in the nozzle chamber 20, and transports the nozzle 34 from the nozzle chamber 20 to the specimen chamber 18. The control device 74 may supply the drying gas to the specimen chamber 18 after the gate valve 16 is opened, and may thus maintain the relationship of the gas pressures between the specimen chamber 18 and the nozzle chamber 20.

In the state before the dropping of the microparticle dispersed liquid drop and during the vacuum-drying, the gate valve 16 is closed, as shown in FIG. 3.

Figure 4:
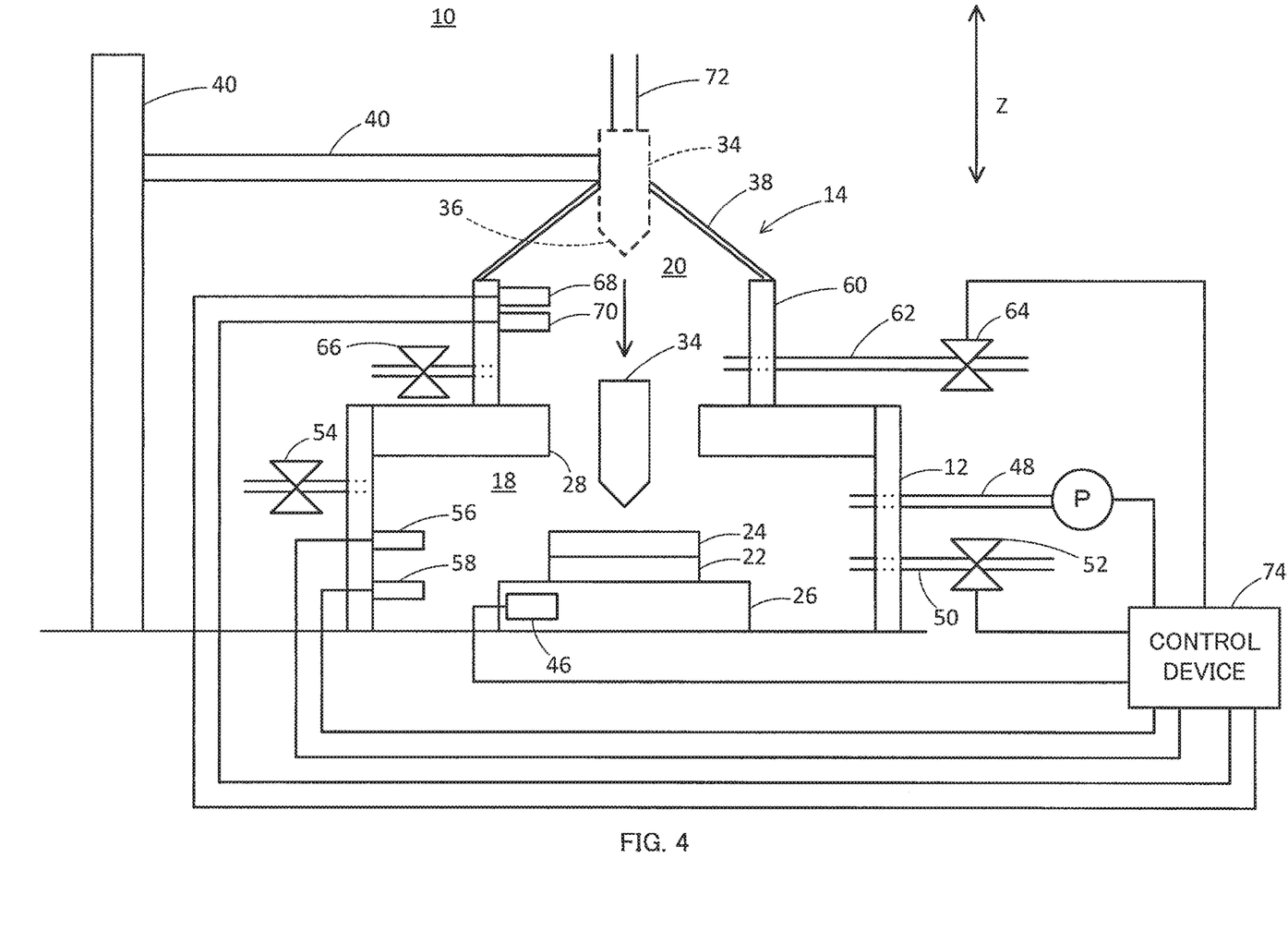
FIG. 4 is a diagram showing the specimen preparation apparatus according to the first embodiment of the present disclosure.

When the microparticle dispersed liquid drop is dropped onto the specimen holder 24, under the control of the control device 74, the gate valve 16 is opened as shown in FIG. 4, and, with this process, the specimen chamber 18 and the nozzle chamber 20 are connected to each other. In this state, under the control of the control device 74, the nozzle 34 is transported from the nozzle chamber 20 into the specimen chamber 18 by the transport mechanism 40. FIG. 4 shows the nozzle 34 transported into the specimen chamber 18 with a solid line. As described above with reference to FIG. 2, with the movement of the nozzle 34, the cover member 38 is deformed. The nozzle 34 is transported until the tip opening 36 of the nozzle 34 is placed near the specimen holder 24. In this state, under the control of the control device 74, the nozzle 34 ejects the microparticle dispersed liquid drop from the tip opening 36 onto the specimen holder 24. With this process, the microparticle dispersed liquid drop is dropped onto the specimen holder 24. For example, under the control of the control device 74, the microparticle dispersed liquid drop may be ejected from the nozzle 34 while the nozzle 34 is moved in the X and Y directions by the transport mechanism 40, so that a plurality of microparticle dispersed liquid drop are dropped onto the specimen holder 24.

An operation of the specimen preparation apparatus 10 during the specimen preparation; that is, a specimen preparation method according to the first embodiment, will now be described in detail with reference to FIGS. 3 and 4.

(1) First, the specimen holder base 22 is placed on the specimen cooling member 26, and the specimen holder 24 is placed on the specimen holder base 22. Next, under the control of the control device 74, in the state where the gate valve 16 is closed as shown in FIG. 3, the pressure inside the specimen chamber 18 is reduced by the pump P, and the inside of the specimen chamber 18 is maintained in the vacuum state.

(2) Next, under the control of the control device 74, the pressure reduction operation by the pump P is stopped, the electromagnetic valves 52 and 64 are opened, and the drying gas is supplied into the specimen chamber 18 and the nozzle chamber 20. It is desirable to not supply the drying gas directly toward the specimen holder base 22 and the specimen holder 24. The temperature and the humidity in the specimen chamber 18 are measured by the temperature and humidity sensor 56, the pressure in the specimen chamber 18 is measured by the pressure sensor 58, and the respective measurement data are output to the control device 74. Similarly, the temperature and the humidity in the nozzle chamber 20 are measured by the temperature and humidity sensor 68, the pressure in the nozzle chamber 20 are measured by the pressure sensor 70, and the respective measurement data are output to the control device 74.

(3) Next, under the control of the controller 74, the electromagnetic valves 52 and 64 are closed, and cooling by the specimen cooling member 26 is started. With this process, supply of the drying gas into the specimen chamber 18 and the nozzle chamber 20 is stopped, and the specimen holder base 22 and the specimen holder 24 are cooled. The temperature of the specimen cooling member 26 is measured by the temperature sensor 46, and the measurement data thereof is output to the control device 74.

(4) With the cooling by the specimen cooling member 26, the temperature of the specimen cooling member 26 is reduced, the ambient temperature in the specimen chamber 18 is reduced, and a gas pressure in the specimen chamber 18 is consequently reduced according to the Boyle-Charles' Law. For example, when the gas pressure in the specimen chamber 18 is 1 atm, and the temperature in the specimen chamber 18 is reduced from 20° C. (293K) to 0° C. (273K), the gas pressure in the specimen chamber 18 becomes 0.93 atm (=273/293). Then, under the control of the control device 74, the electromagnetic valve 52 at the side of the specimen chamber 18 is opened, and the drying gas is supplied into the specimen chamber 18. In this process, the electromagnetic valve 52 is controlled and the flow rate of the drying gas supplied into the specimen chamber 18 is adjusted such that the gas pressure in the specimen chamber 18 is higher than the gas pressure in the nozzle chamber 20. For example, the control device 74 adjusts the flow rate of the drying gas supplied into the specimen chamber 18 based on the measurement data of the pressure sensors 58 and 70, such that the gas pressure in the specimen chamber 18 is higher than the gas pressure in the nozzle chamber 20. The drying gas may be supplied into the specimen chamber 18 before start of cooling by the specimen cooling member 26, and the cooling by the specimen cooling member 26 may then be started, or, alternatively, the drying gas may be supplied into the specimen chamber 18 at the same time as the start of the cooling by the specimen cooling member 26.

(5) When the specimen cooling member 26 is cooled, the temperature of the specimen cooling member 26 becomes lower than or equal to a preset threshold temperature, and the gas pressure in the specimen chamber 18 is higher than the gas pressure in the nozzle chamber 20, as shown in FIG. 4, under the control of the control device 74, the gate valve 16 is opened. The threshold temperature is, for example, a temperature in a range of −40° C.~−20° C. Alternatively, the threshold temperature may be a temperature other than one in this temperature range.

(6) When the gate valve 16 is opened, the drying gas flows from inside of the specimen chamber 18 into the nozzle chamber 20 by a difference (gas pressure difference) between the gas pressure in the specimen chamber 18 and the gas pressure in the nozzle chamber 20. With this process, it becomes possible to prevent or suppress intrusion of warm air in the nozzle chamber 20 into the specimen chamber 18, and to consequently prevent or suppress contact with the specimen holder base 22, the specimen holder 24, and the specimen cooling member 26. As a result, it becomes possible to prevent occurrence of dew condensation at the specimen cooling member 26, the specimen holder base 22, and the specimen holder 24. In other words, as described above, due to the reduction of the temperature in the specimen chamber 18, the gas pressure in the specimen chamber 18 is reduced, and, consequently, warm air attempts to enter the specimen chamber 18 from the inside of the nozzle chamber 20. However, in the present embodiment, with the supply of the drying gas, there is maintained a state in which the gas pressure in the specimen chamber 18 is higher than the gas pressure in the nozzle chamber 20. Because of this, the intrusion of the warm air into the specimen chamber 18 can be prevented or suppressed. As a result, occurrence of dew condensation at the specimen holder base 22, the specimen holder 24, and the specimen cooling member 26 can be prevented.

(7) Next, under the control of the control device 74, as shown in FIG. 4, the nozzle 34 is lowered by the transport mechanism 40, to place the tip opening 36 of the nozzle 34 near the specimen holder 24. In this state, under the control of the control device 74, the nozzle 34 ejects the microparticle dispersed liquid drop from the tip opening 36 onto the specimen holder 24. With this process, the microparticle dispersed liquid drop is dropped onto the specimen holder 24. For example, while the nozzle 34 is moved in the X and Y directions by the transport mechanism 40, the microparticle dispersed liquid drop is ejected from the nozzle 34, and a plurality of microparticle dispersed liquid drops are dropped onto the specimen holder 24. While the gate valve 16 is in the open state, the electromagnetic valve 52 is opened under the control of the control device 74, and the drying gas continues to be supplied into the specimen chamber 18. With this process, the pressure difference between the inside of the specimen chamber 18 and the inside of the nozzle chamber 20 can be more reliably maintained.

(8) When the dropping process of the microparticle dispersed liquid drop by the nozzle 34 is completed, under the control of the control device 74, the nozzle 34 is elevated by the transport mechanism 40 as shown in FIG. 3, the nozzle 34 is placed in the nozzle chamber 20, and the gate valve 16 is closed.

(9) Because the specimen holder 24 is cooled by the specimen cooling member 26, the microparticle dispersed liquid drop dropped onto the specimen holder 24 is frozen.

(10) Next, under the control of the control device 74, the electromagnetic valve 52 is closed, the supply of the drying gas into the specimen chamber 18 is stopped, and the pressure in the specimen chamber 18 is reduced by the vacuum pump P. With this process, the inside of the specimen chamber 18 is set in a vacuum state, and vacuum-drying is executed. In the vacuum-drying, the solvent of the microparticle dispersed liquid drop evaporates, (the frozen solvent sublimates), and the microparticle remains on the specimen holder 24. The remaining microparticle is used as the specimen for the microscope. Alternatively, depending on the observation condition by the microscope, the solvent may also remain.

(11) When the solvent of the microparticle dispersed liquid drop is evaporated (sublimated), and the specimen of the microparticle is prepared, under the control of the control device 74, the specimen cooling member 26 is warmed. For example, the specimen cooling member 26 may be warmed by the specimen cooling member 26 itself (for example, a Peltier element), or the specimen cooling member 26 may be warmed by a heater or the like. For example, the specimen cooling member 26 is warmed to room temperature (for example, about 25° C.). With this process, the temperatures of the specimen holder base 22, the specimen holder 24, and the microparticle specimen are increased to about room temperature. In this manner, by warming the specimen holder base 22 or the like to room temperature, occurrence of dew condensation when the specimen is taken out can be prevented.

(12) Next, under the control of the control device 74, the pressure reduction process by the vacuum pump P is stopped, the electromagnetic valve 52 is opened, and the drying gas is supplied into the specimen chamber 18. For example, the drying gas is supplied into the specimen chamber 18 until the gas pressure in the specimen chamber 18 becomes the atmospheric pressure.

(13) After the temperature of the specimen cooling member 26 is maintained at the room temperature and the gas pressure in the specimen chamber 18 is maintained at the atmospheric pressure, the specimen holder 24 is taken out from the specimen chamber 18. With this process, the microparticle serving as the specimen is taken out. With these processes, the preparation of the microparticle specimen is completed.

As described, in the first embodiment, when the microparticle dispersed liquid drop is dropped from the nozzle 34 onto the specimen holder 24, a state is maintained in which the gas pressure in the specimen chamber 18 is higher than the gas pressure in the nozzle chamber 20. With this configuration, it becomes possible to prevent or suppress intrusion of warm air from the nozzle chamber 20 into the specimen chamber 18, and, as a result, occurrence of the dew condensation at the specimen holder base 22, the specimen holder 24, and the specimen cooling member 26 can be prevented. Because of this, it becomes possible to prevent contamination of the microparticle specimen caused by the dew condensation.

In addition, by providing the frame 60, it becomes possible to prevent entry and dragging of the cover member 38 into the specimen chamber 18 when the nozzle 34 is transported to the inside of the specimen chamber 18.

Alternatively, the inside of the specimen chamber 18 may be imaged by the camera 32, and the operator may observe the inside of the specimen chamber 18 with the image obtained by the camera 32. For example, when the operator confirms a sign of dew condensation around the specimen cooling member 26, the operator may command to increase the amount of supply of the drying gas into the specimen chamber 18. The control device 74, in response to the command, increases the amount of supply of the drying gas into the specimen chamber 18. With this process, it becomes possible to prevent occurrence of the dew condensation at the periphery of the specimen cooling member 26.

Alternatively, the control device 74 may control the amount of supply of the drying gas into the specimen chamber 18 (that is, the degree of opening of the electromagnetic valve 52) based on the measurement data (temperature and humidity) obtained by the temperature and humidity sensor 56. For example, the control device 74 may control the amount of supply of the drying gas into the specimen chamber 18 so that the humidity in the specimen chamber 18 (for example, relative humidity) is lower than or equal to a preset target humidity. For example, the control device 74 may control the amount of supply of the drying gas into the specimen chamber 18 such that the relative humidity (amount of water vapor A of the ambience in the specimen chamber 18/saturation amount of water vapor C in the ambience) is lower than or equal to a target relative humidity (saturation amount of water vapor B in the specimen cooling member 26/saturation amount of water vapor C in the ambience).

Second Embodiment

Figure 5:
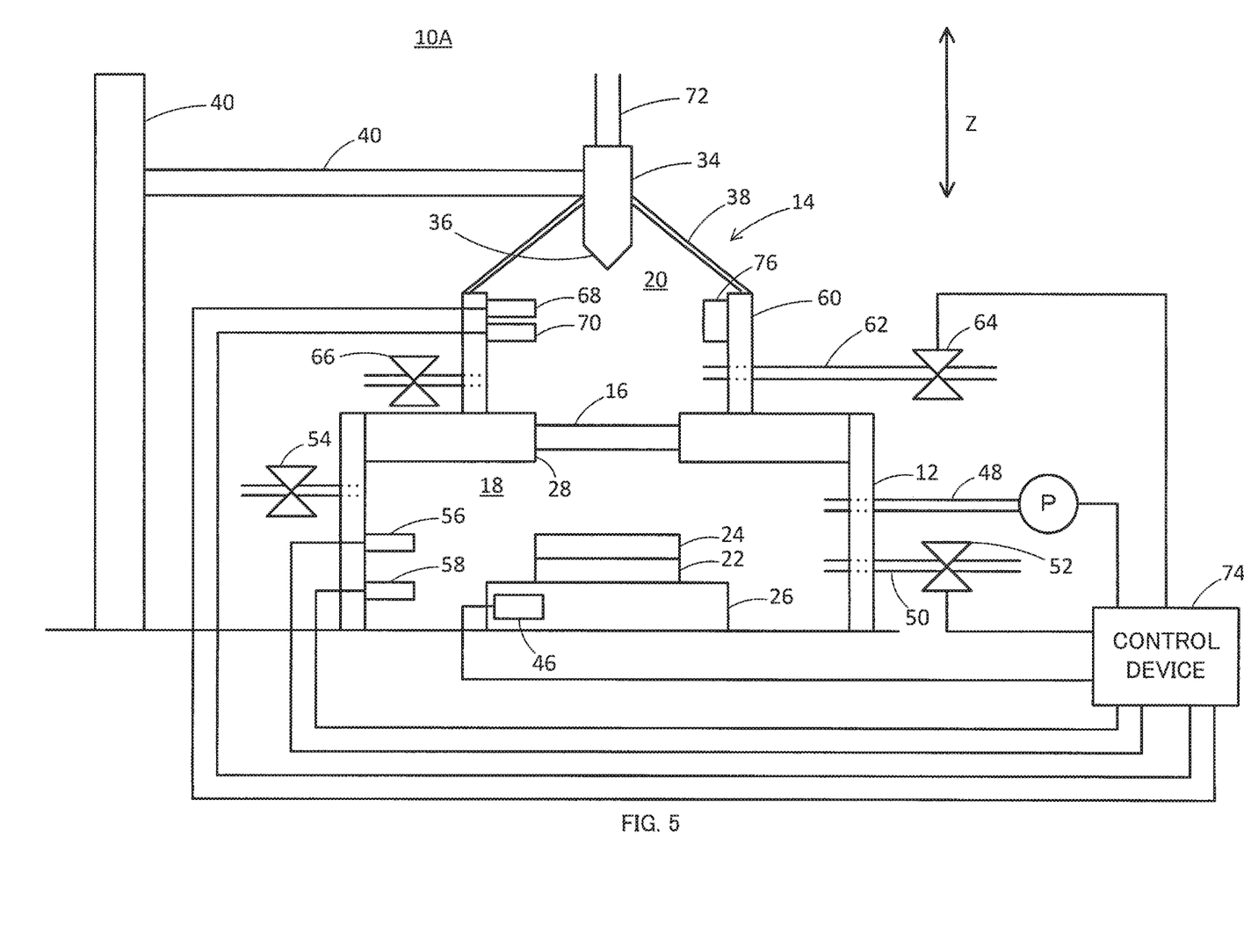
FIG. 5 is a diagram showing a specimen preparation apparatus according to a second embodiment of the present disclosure.

A specimen preparation apparatus 10A according to a second embodiment of the present disclosure will now be described with reference to FIG. 5. FIG. 5 shows a structure of the specimen preparation apparatus 10A according to the second embodiment of the present disclosure.

The specimen preparation apparatus 10A according to the second embodiment of the present disclosure includes the structures of the specimen preparation apparatus 10 according to the first embodiment shown in FIG. 3, and further comprises a cooling member 76. The cooling member 76 is placed, for example, in the nozzle chamber 20 and on an inner side surface of the frame 60. The cooling member 76 is a member for reducing the temperature in the nozzle chamber 20, and reduces the temperature in the nozzle chamber 20 using, for example, a Peltier element. Alternatively, the temperature in the nozzle chamber 20 may be reduced using other methods. In the second embodiment, the control device 74 further controls the cooling operation by the cooling member 76.

In the second embodiment, the inside of the nozzle chamber 20 is cooled by the cooling member 76. By the temperature in the nozzle chamber 20 being reduced, the gas pressure in the nozzle chamber 20 is reduced. With this process, it becomes possible to prevent or suppress a state that the gas pressure in the nozzle chamber 20 is higher than the gas pressure in the specimen chamber 18.

An operation of the specimen preparation apparatus 10A during the specimen preparation; that is, a specimen preparation method in the second embodiment, will now be described.

(21) First, the specimen holder base 22 is placed on the specimen cooling member 26, and the specimen holder 24 is placed on the specimen holder base 22. Then, under the control of the control device 74, in a state where the gate valve 16 is closed, the pressure in the specimen chamber 18 is reduced by the pump P, and the inside of the specimen chamber 18 is maintained in a vacuum state.

(22) Next, under the control of the control device 74, the pressure reduction operation by the pump P is stopped, the electromagnetic valves 52 and 64 are opened, and the drying gas is supplied into the specimen chamber 18 and the nozzle chamber 20. The temperature and the humidity in the specimen chamber 18 are measured by the temperature and humidity sensor 56, the pressure in the specimen chamber 18 is measured by the pressure sensor 58, and the respective measurement data are output to the control device 74. Similarly, the temperature and the humidity in the nozzle chamber 20 are measured by the temperature and humidity sensor 68, the pressure in the nozzle chamber 20 is measured by the pressure sensor 70, and the respective measurement data are output to the control device 74.

(23) Next, under the control of the control device 74, the electromagnetic valves 52 and 64 are closed, and cooling by the specimen cooling member 26 and cooling by the cooling member 76 are started. With this process, the supply of the drying gas into the specimen chamber 18 and the nozzle chamber 20 is stopped, the specimen holder base 22 and the specimen holder 24 are cooled by the specimen cooling member 26, and the inside of the nozzle chamber 20 is cooled by the cooling member 76.

(24) With the cooling by the specimen cooling member 26, the temperature of the specimen cooling member 26 is reduced, and, consequently, the ambient temperature in the specimen chamber 18 is reduced, and the gas pressure in the specimen chamber 18 is reduced according to the Boyle-Charles' Law. Similarly, with the cooling by the cooling member 76, the temperature of the cooling member 76 is reduced, and, consequently, the ambient temperature in the nozzle chamber 20 is reduced, and the gas pressure in the nozzle chamber 20 is reduced according to the Boyle-Charles' Law. In this process, under the control of the control device 74, the temperature in the nozzle chamber 20; that is, the cooling operation of the cooling member 76, is controlled such that the gas pressure in the specimen chamber 18 is higher than the gas pressure in the nozzle chamber 20; that is, the gas pressure in the nozzle chamber 20 is lower than the gas pressure in the specimen chamber 18. For example, the control device 74 controls the cooling operation of the cooling member 76 based on the measurement data of the pressure sensors 58 and 70 such that the gas pressure in the nozzle chamber 20 is lower than the gas pressure in the specimen chamber 18. As an alternative configuration, the control device 74 may control the cooling operation of the cooling member 76 based on the measurement data of the temperature and humidity sensor 56 in the specimen chamber 18 and the measurement data of the temperature and humidity sensor 68 in the nozzle chamber 20 such that the gas pressure in the nozzle chamber 20 is lower than the gas pressure in the specimen chamber 18. For example, in the case where the gas pressure in the specimen chamber 18 is 1 atm and the temperature of the specimen chamber 18 is reduced from 20° C. to 0° C., the gas pressure in the specimen chamber 18 becomes 0.93 atm. In order to set the gas pressure in the nozzle chamber 20 to a pressure lower than 0.93 atm, the temperature in the nozzle chamber 20 is reduced to a temperature lower than 0° C. (273K). In this case, the control device 74 controls the cooling operation of the cooling member 76 such that the temperature in the nozzle chamber 20 is lower than 0° C.

(25) When the specimen cooling member 26 and the cooling member 76 are cooled, the temperature of the specimen cooling member 26 becomes lower than a preset temperature threshold, and the gas pressure in the specimen chamber 18 is higher than the gas pressure in the nozzle chamber 20, the gate valve 16 is opened under the control of the control device 74. When a difference (gas pressure difference) between the gas pressure in the specimen chamber 18 and the gas pressure in the nozzle chamber 20 before the gate valve 16 is opened is small or zero, the electromagnetic valve 52 may be opened in advance and the drying gas may be supplied into the specimen chamber 18 under the control of the control device 74, such that the gas pressure in the specimen chamber 18 is higher than the gas pressure in the nozzle chamber 20. Alternatively, even when the gas pressure difference is large, the drying gas may be supplied into the specimen chamber 18 before the gate valve 16 is opened while the inside of the nozzle chamber 20 is cooled by the cooling member 76, such that the gas pressure in the specimen chamber 18 is higher than the gas pressure in the nozzle chamber 20.

(26) When the gate valve 16 is opened, the drying gas flows from inside of the specimen chamber 18 into the nozzle chamber 20 due to the difference (gas pressure difference) between the gas pressure in the specimen chamber 18 and the gas pressure in the nozzle chamber 20. With this process, it becomes possible to prevent or suppress intrusion of the air in the nozzle chamber into the specimen chamber 18, and to consequently prevent or suppress contact of the air with the specimen holder base 22, the specimen holder 24, and the specimen cooing member 26. As a result, occurrence of the dew condensation at the specimen cooling member 26, the specimen holder base 22, and the specimen holder 24 can be prevented.

(27) Next, under the control of the control device 74, the nozzle 34 is lowered by the transport mechanism 40, and the tip opening 36 of the nozzle 34 is placed near the specimen holder 24. In this state, under the control of the control device 74, the nozzle 34 ejects the microparticle dispersed liquid drop from the tip opening 36 onto the specimen holder 24. As a result, the microparticle dispersed liquid drop is dropped onto the specimen holder 24. During this process, the temperature of the cooing member 76 in the nozzle chamber 20 may be set lower than the temperature of the specimen cooling member 26. With this configuration, even if the air in the nozzle chamber 20 intrudes the specimen chamber 18 due to convection or the like, the cooling member 76 functions as a cold trap, which is useful in preventing occurrence of the dew condensation at the specimen holder base 22 or the like. Alternatively, the electromagnetic valve 52 may be opened under the control of the control device 74, and supply of the drying gas into the specimen chamber 18 may be continued. With such a configuration, the pressure difference between the inside of the specimen chamber 18 and the inside of the nozzle chamber 20 can be more reliably maintained.

(28) When the liquid dropping process of the microparticle dispersed liquid drop by the nozzle 34 is completed, under the control of the control device 74, the nozzle 34 is elevated by the transport mechanism 40, the nozzle 34 is placed in the nozzle chamber 20, and the gate valve 16 is closed.

(29) Because the specimen holder 24 is cooled by the specimen cooling member 26, the microparticle dispersed liquid drop dropped onto the specimen holder 24 is frozen.

(30) Next, under the control of the control device 74, the electromagnetic valve 52 is closed, the supply of the drying gas into the specimen chamber 18 is stopped, and the pressure in the specimen chamber 18 is reduced by the vacuum pump P. With this process, the inside of the specimen chamber 18 is set in a vacuum state, the vacuum-drying is executed, and, as a result, the microparticle serving as the specimen remains on the specimen holder 24.

(31) When the solvent of the microparticle dispersed liquid drop evaporates (sublimates) and the specimen of the microparticle is prepared, the specimen cooling member 26 is warmed to, for example, room temperature, under the control of the control device 74.

(32) Next, after the specimen cooling member 26 is maintained at room temperature and the specimen chamber 18 is maintained at atmospheric pressure, the specimen holder 24 is taken out from the specimen chamber 18. With this process, the microparticle serving as the specimen is taken out. With these processes, the preparation of the microparticle specimen is completed.

As described, in the second embodiment also, similar to the first embodiment, there is maintained a state in which the gas pressure in the specimen chamber 18 is higher than the gas pressure in the nozzle chamber 20, and the intrusion of the air from the nozzle chamber 20 into the specimen chamber 18 can be prevented or suppressed. Because of this, occurrence of dew condensation at the specimen holder base 22, the specimen holder 24, and the specimen cooling member 26 can be prevented, and contamination of the microparticle specimen can be prevented.

Third Embodiment

Figure 6:
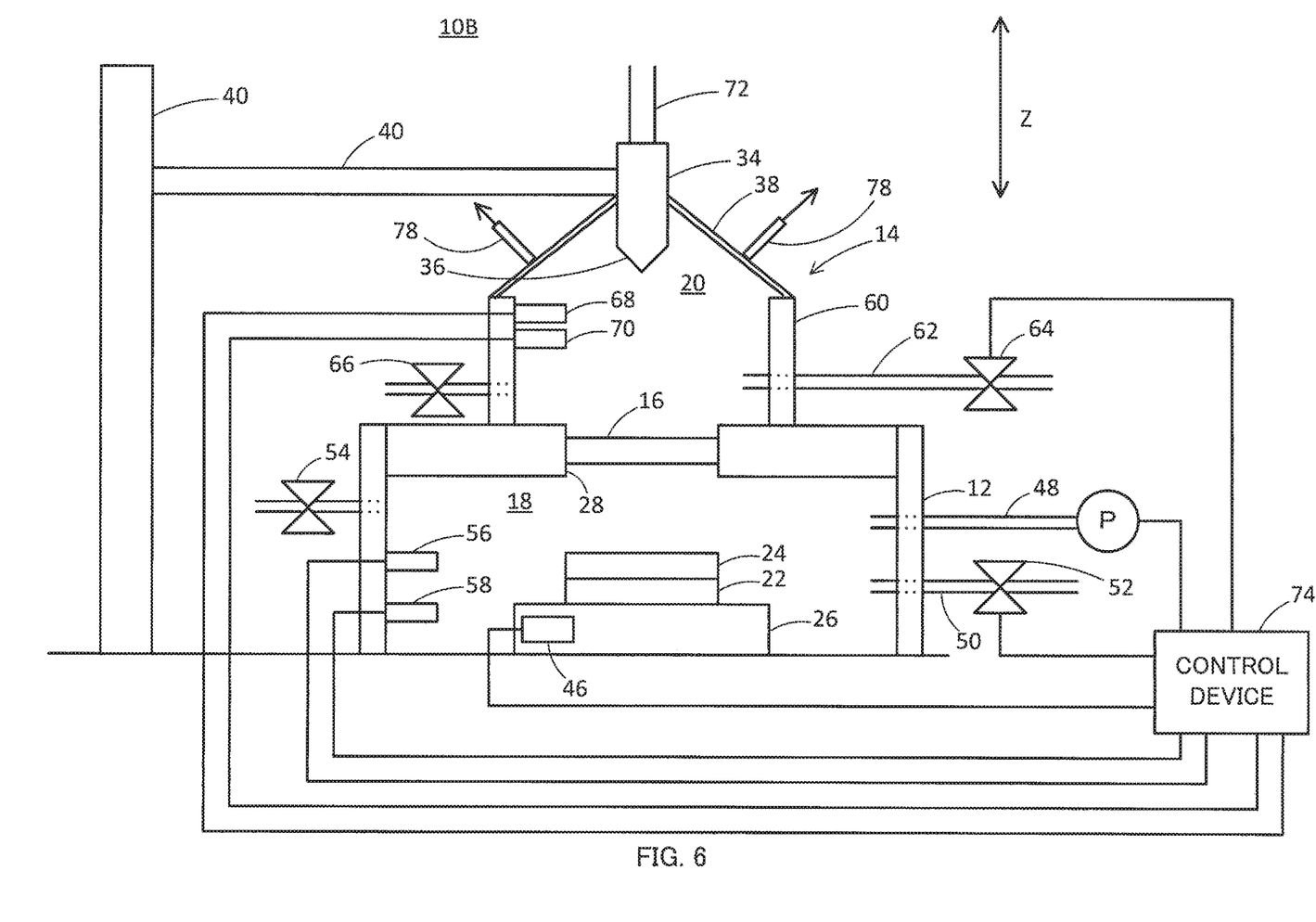
FIG. 6 is a diagram showing a specimen preparation apparatus according to a third embodiment of the present disclosure.

A specimen preparation apparatus 10B according to a third embodiment of the present disclosure will now be described with reference to FIG. 6. FIG. 6 shows a structure of the specimen preparation apparatus 10B according to the third embodiment of the present disclosure.

The specimen preparation apparatus 10B according to the third embodiment includes the structures of the specimen preparation apparatus 10 of the first embodiment shown in FIG. 3, and further comprises a cover support member 78. The cover support member 78 is placed on a surface at an outer side (outer side of the nozzle chamber 20) of the cover member 38, and, for example, a member such as a string or a rubber member having elasticity is attached. With the cover support member 78 being pulled in an outer direction of the nozzle chamber 20 by the string, rubber member, or the like, a tension force thereof is applied to the cover member 38, and the cover member 38 is pulled in the outer direction of the nozzle chamber 20. With this configuration, it becomes possible to prevent entry or dragging of the cover member 38 into the specimen chamber 18 when the nozzle 34 is transported into the specimen chamber 18.

An operation of the specimen preparation apparatus 10B in the specimen preparation; that is, a specimen preparation method according to the third embodiment, is identical to the operation of the specimen preparation apparatus 10 of the first embodiment; that is, the specimen preparation method of the first embodiment, and thus will not be described again.

The specimen preparation apparatus 10B of the third embodiment may comprise the cooling member 76 similar to the specimen preparation apparatus 10A of the second embodiment. In this case, the operation of the specimen preparation apparatus 10B of the third embodiment; that is, the specimen preparation method of the third embodiment, is identical to the operation of the specimen preparation apparatus 10A of the second embodiment; that is, the specimen preparation method of the second embodiment. Thus, the operation in this case also will not be described.

As an alternative configuration, the frame 60 may be omitted in the specimen preparation apparatus 10B. In this case also, because the cover member 38 is pulled in the outer direction of the nozzle chamber 20 by the tension force through the cover support member 78, the entry and dragging of the cover member 38 into the specimen chamber 18 can be prevented.

The invention claimed is:

1. A specimen preparation apparatus comprising:
a lower-side structure that forms a specimen chamber in which a specimen base is provided, the lower-side structure comprising:
   a first gas pipe in communication with a supply gas and configured to release the supply gas to the specimen chamber; and
   a vacuum pipe in communication with a vacuum source and configured to remove gas from the specimen chamber;
an upper-side structure that forms a nozzle chamber above the specimen chamber, the upper-side structure comprising:
   a second gas pipe in communication with the supply gas and configured to release the supply gas to the nozzle chamber;
   a relief valve configured to remove gas from the nozzle chamber; and
   a nozzle comprising a nozzle tip configured to eject a specimen;
the specimen base further comprising a cooler that cools the specimen base;
a gate valve that separates the specimen chamber and the nozzle chamber;
a controller; and
memory storing programming instructions configured to control the controller to maintain a relationship of gas pressures such that a gas pressure in the specimen chamber is higher than a gas pressure in the nozzle chamber when the specimen chamber and the nozzle chamber are in communication with each other by at least:
   controlling release of the supply gas into the specimen chamber through the first gas pipe inlet;
   controlling removal of gas from the specimen chamber through the vacuum pipe;
   controlling introduction of the supply gas into the nozzle chamber through the second gas pipe; and
   controlling transfer of gas between the specimen chamber and the nozzle chamber through the gate valve,
wherein the controller is further programmed or configured to control the gas pressure such that the gas pressure in the specimen chamber is higher than the gas pressure in the nozzle chamber after the specimen base is cooled by the cooler and before the gate valve is opened and to open the gate valve in response to the specimen base having a temperature equal to or lower than a preset threshold temperature and the gas pressure in the specimen chamber being higher than the gas pressure in the nozzle chamber.

2. The specimen preparation apparatus according to claim 1, wherein the controller is further programmed or configured to control the nozzle to eject the specimen onto the specimen base when the lower-side structure and the upper-side structure are in communication with each other.

3. The specimen preparation apparatus according to claim 1, wherein the controller is further programmed or configured to control introduction of the supply gas into the specimen chamber by controlling a valve positioned in the first gas pipe, such that the gas pressure in the specimen chamber is higher than the gas pressure in the nozzle chamber.

4. The specimen preparation apparatus according to claim 3, wherein the controller and the relief valve maintain the relationship of the gas pressures between the specimen chamber and the nozzle chamber by controlling the introduction of the supply gas into the specimen chamber and controlling the removal of the supply gas from the nozzle chamber after the gate valve is opened.

5. The specimen preparation apparatus according to claim 1, further wherein
the vacuum source in communication with the vacuum pipe of the specimen chamber is configured to reduce the pressure in the specimen chamber, wherein
the controller is further programmed or configured to open the gate valve after:
   reducing the pressure in the specimen chamber by the vacuum source,
   cooling the specimen base by the cooler,
   introducing the supply gas into the specimen chamber, and then
   forming the relationship of the gas pressures between the specimen chamber and the nozzle chamber, in a state where the gate valve is closed.

6. The specimen preparation apparatus according to claim 1, further comprising
a transport mechanism that transports the nozzle between the upper-side structure and the lower-side structure, wherein
the upper-side structure comprises a cover member that deforms with a movement of the nozzle.

7. The specimen preparation apparatus according to claim 6, further comprising
a rigid frame that is placed to surround an opening of the gate valve at a periphery of the gate valve, wherein
the cover member seals from an opening edge of the frame to a periphery of the nozzle.

8. The specimen preparation apparatus according to claim 1, wherein the controller is further programmed or configured to control a process of ejecting the specimen onto the specimen base by the nozzle, closing the gate valve after the process of ejecting the specimen onto the specimen base by the nozzle, and a process of executing vacuum-drying by reducing the pressure in the specimen chamber after the specimen is ejected onto the specimen base.

* * * * *

UNITED STATES PATENT AND TRADEMARK OFFICE
CERTIFICATE OF CORRECTION

| | | |
|---|---|---|
| PATENT NO. | : 11,231,346 B2 | Page 1 of 1 |
| APPLICATION NO. | : 15/873246 | |
| DATED | : January 25, 2022 | |
| INVENTOR(S) | : Satoru Akai et al. | |

It is certified that error appears in the above-identified patent and that said Letters Patent is hereby corrected as shown below:

On the Title Page

Column 2, item (56) Other Publications, Line 3, delete "Miscroscopy"," and insert -- Microscopy", --

Column 2, item (56) Other Publications, Line 4, delete "Histrochemistry" and insert
-- Histochemistry --

Signed and Sealed this
Third Day of May, 2022

Katherine Kelly Vidal
*Director of the United States Patent and Trademark Office*